US00PP16892P2

(12) United States Plant Patent
Utecht

(10) Patent No.: US PP16,892 P2
(45) Date of Patent: Jul. 25, 2006

(54) ***PELARGONIUM* PLANT NAMED 'FISMOPINK'**

(50) Latin Name: *Pelargonium×hortorum*
Varietal Denomination: Fismopink

(75) Inventor: Angelika Utecht, Montabaur (DE)

(73) Assignee: Florfis AG, Binningen (CH)

( * ) Notice: Subject to any disclaimer, the term of this patent is extended or adjusted under 35 U.S.C. 154(b) by 15 days.

(21) Appl. No.: 11/167,679

(22) Filed: Jun. 27, 2005

(51) Int. Cl.
*A01H 5/00* (2006.01)

(52) U.S. Cl. ..... Plt./325

(58) Field of Classification Search ..... Plt./325
See application file for complete search history.

*Primary Examiner*—Kent Bell
(74) *Attorney, Agent, or Firm*—Jondle & Associates P.C.

(57) ABSTRACT

A new cultivar of *Pelargonium* particularly distinguished by its light pink to nearly white single-type flowers having a pattern of cherry-red stripes and dots, large inflorescences, large leaves with distinct zonation, rounded and well-branched plant habit, and its late spring flowering response is disclosed.

1 Drawing Sheet

Figure 1:
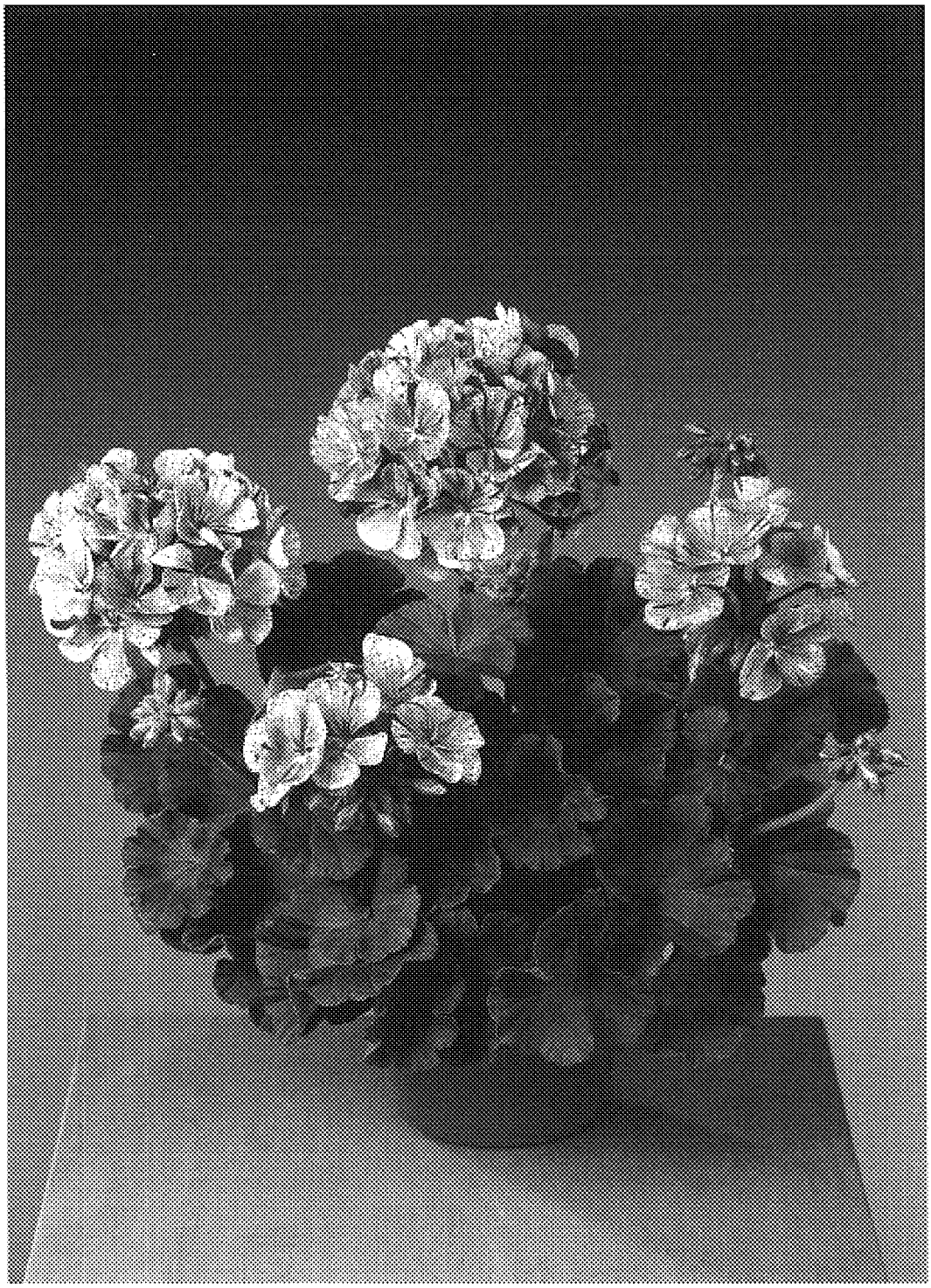

Genus and species: *Pelargonium×hortorum.*
Variety denomination: 'Fismopink'.

BACKGROUND OF THE NEW PLANT

The present invention comprises a new and distinct cultivar of *Pelargonium,* botanically known as *Pelargonium× hortorum,* resp. a hybrid of *Pelargonium zonale* L'Héritier and hereinafter referred to by the cultivar name 'Fismopink'. The new cultivar is a product of a planned breeding program which had the objective of creating new varieties having bi-colored flowers and good outdoor performance. 'Fismopink' was discovered as a seedling resulting from a cross between the female parent, 'Starburst Violet Rose' (U.S. Plant Pat. No. 11,394, 'BFP-1561'), which has deep violet-pink, single-type flowers, and the male parent, hybrid seedling No. i95/0109/21 (unpatented), which has purple-pink, single type flowers.

The new cultivar was created in 2000 in Hillscheid, Germany, and has been asexually reproduced repeatedly by vegetative cuttings in Galdar, Gran Canaria, Spain, and Hillscheid, Germany, over a four year period. 'Fismopink' has not been observed under all possible environmental conditions, thus, the phenotype may vary significantly with variations in the environment such as temperature, light intensity, and day length. It has been found to retain its distinctive characteristics through successive asexual propagations. 'Fismopink' reproduces true to type in successive generations of asexual reproduction.

SUMMARY OF THE INVENTION

The following are the most outstanding and distinguishing characteristics of this new cultivar when grown under normal horticultural practices in Hillscheid, Germany.

1. Light pink to white, single-type flowers with cherry-red stripes and dots;
2. Large inflorescences on strong peduncles high above the foliage;
3. Medium-green foliage and large leaves with distinct zonation;

4. Medium to tall, with a rounded and well-branched plant habit;
5. Mid to moderately late season flowering response; and
6. Good rain resistance.

DESCRIPTION OF PHOTOGRAPH

This new *geranium* plant is illustrated by the accompanying photograph which shows blooms, buds, and foliage of the plant; the colors shown are as true as can be reasonably obtained by conventional photographic procedures. The photograph is of a twelve-week-old plant grown from rooted cuttings, in 14-cm pots, left un-pinched, and grown under greenhouse conditions which approximate those generally used in commercial practice.

FIG. 1 shows overall plant habit including blooms, buds, and foliage.

DESCRIPTION OF THE NEW CULTIVAR

The following detailed descriptions set forth the distinctive characteristics of 'Fismopink'. The data which define these characteristics were collected from asexual reproductions carried out in Hillscheid, Germany. The plant history was taken on twelve-week-old, un-pinched plants in 14-cm pots in a greenhouse during mid-May. The color readings were determined under natural light in mid-May from flowers grown in a greenhouse. Color references are to The R.H.S. Colour Chart of The Royal Horticultural Society of London (R.H.S.) (2001).

DETAILED BOTANICAL DESCRIPTION

Classification:

*Botanical.*—*Pelargonium×hortorum,* resp. a hybrid of *Pelargonium zonale* L'Héritier.

*Common name.*—*Geranium.*

*Parentage.*—Female parent: 'Starburst Violet Rose' (U.S. Plant Pat. No. 11,394, 'BFP-1561'). Male parent: Hybrid seedling No. i95/0109/21 (unpatented).

Plant:

*Form.*—Rounded.

*Branching habit.*—4.8 branches per plant.

*Height.*—14.2 cm for a 9 week-old plant (measured from base of stem to the tips of the branches, excluding the inflorescences).

*Width.*—24.2 cm for a 9 week-old plant.

*Time to produce a finished flowering plant.*—For spring flower response in Hillscheid, Germany, in 2004, 50% of the plants had open flowers after 9 weeks.

*Outdoor plant performance.*—Plants continuously flower; a flower count in mid-May of 2004 in Hillscheid, Germany indicated about 2 inflorescences per plant.

Leaves:

*Arrangement.*—Alternate.

*Immature leaf.*—Color: Upper surface: RHS 137C (medium-green). Lower surface: RHS 137D (medium-green).

*Mature leaf.*—Color: Upper surface: RHS 137C (medium green). Lower surface: RHS 137D. Length: 6.5 cm. Width: 10.5 cm.

*Zonation color.*—RHS 166A (brown).

*Zonation diameter.*—Inner ring is 5.3 cm while belt of zonation is 2.5 cm wide.

*Apex.*—Rounded.

*Base.*—Cordate.

*Shape.*—Kidney-shaped with only very weak lobes and with open gap between the lowest lobes.

*Margin.*—Bi-crenate, somewhat wavy.

*Texture.*—Upper surface is smooth, dull, and velvety.

Petioles:

*Length.*—5.0–6.0 cm.

*Diameter.*—0.35 cm.

*Color.*—RHS 143B to RHS 143C.

*Texture.*—Very short pubescence.

Stems:

*Length.*—6.0–9.0 cm.

*Internode length.*—1.5–2.5 cm.

*Color.*—RHS 143D (light-green).

*Texture.*—Appears smooth but is covered by weak pubescence.

Flower buds:

*Length.*—2.2 cm.

*Width.*—0.8 cm.

*Shape.*—Narrow and elliptical.

*Color of sepals* (*just before petals unfold*).—RHS 143A (green).

*Color of petals* (*just before petals unfold*).—Pale pink to white, RHS 69D to RHS 155A, red-purple markings same as on the lower side of petals.

Inflorescence:

*Type.*—An umbel composed of 25–35 flowers.

*Umbel diameter.*—10.3 cm.

*Umbel depth* (*height*).—6.5 cm.

*Umbel shape.*—Semi-spherical.

*Lastingness of umbel on the plant.*—16–18 days.

*Peduncle.*—Length: 14.8 cm. Diameter: 5.0 mm. Texture: Very short pubescence. Color: RHS 143A (green) with a slight tinge of RHS 179A (brown) to RHS 179B (brown).

*Pedicel.*—Length: 2.8 cm, with spur. Diameter: 1.5 mm. Texture: Very short pubescence. Color: RHS 143B (light green) near upper end and weakly brownish infused, from RHS 179A to RHS 179B.

Corolla:

*Diameter.*—4.8 cm.

*Form.*—Single-type.

*Shape.*—Round outline, wide open cup-shape, occasionally with a gap separating upper petals from lower petals.

*Number of petals.*—5.

*Number of petaloids.*—None.

*Lastingness of individuals flowers on the plant.*—6–8 days at 18° C.

*Fragrance.*—None.

Petals:

*Upper petals.*—Length: 3.1–3.2 cm. Width: 2.1–2.2 cm. Color: Upper surface: Mainly RHS 57D; lighter near margins, from RHS 155D to RHS 69D. Lower surface: Nearly RHS 69D (white), RHS 52D near the bases of the upper petals, and RHS N66B irregularly spread fine streaks. Markings: RHS 43C spots near the bases and RHS N66A (red-purple) stripes and dots.

*Lower petals.*—Length: 2.7–2.8 cm. Width: 2.5 cm. Color: Upper surface: Mainly RHS 57D but lighter near margins, from RHS 155D to RHS 69D. Lower surface: Nearly RHS 69D (white), RHS 52D near the bases of the upper petals, and RHS N66B irregularly spread fine streaks. Markings: RHS N66A (red-purple) stripes and dots.

*Shape.*—Mostly obovate.

*Apex.*—Rounded.

*Base.*—Acute.

*Margin.*—Entire.

*Texture.*—Smooth, glabrous, and slightly glossy.

Sepals:

*Number.*—5.

*Length.*—1.0–1.2 cm.

*Width.*—0.4–0.5 cm for largest upper sepal, 0.3–0.4 cm for the other sepals.

*Shape.*—Linear to lanceolate.

*Apex.*—Acute.

*Base.*—Truncate.

*Margin.*—Entire.

*Texture.*—Weak pubescence.

*Color.*—RHS 143B (light green) is uniform for both upper and lower surface.

Reproductive organs:

*Androecium.*—Number of anthers: 5–7. Filament color: RHS 155D (white) to RHS 46C (red) near upper end. Filament length: 0.5 cm. Pollen color: RHS 28A (yellow-orange). Pollen amount: Moderate.

*Gynoecium.*—Pistil number: 1. Pistil length: 0.8 cm. Stigma color: RHS 41A (scarlet). Stigma shape: 5-lobed. Style color: RHS 41B. Style length: 0.3 cm. Style shape: Filiform, filament-like, with the lobes of the stigma at right from the upper end.

Fruit/seed set: No seed set observed.

Disease and insect resistance: Average/typical for the species.

COMPARISON WITH KNOWN CULTIVARS

Of the many commercial cultivars known to the present inventor, the most similar in comparison to 'Fismopink' are the varieties 'Starburst Violet Rose' (U.S. Plant Pat. No. 11,394, 'BFP-1561') and the 'Amri Conred' (U.S. Plant Pat. No. 15,880).

Cultivar 'Fismopink' differs from the female parent 'Starburst Violet Rose' (U.S. Plant Pat. No. 11,394, 'BFP-1561')

in that it has larger inflorescences, the striped pattern on pattern is more reddish and less blue in hue, the zonation on the leaves is somewhat stronger, and the growth habit is generally more vigorous.

Cultivar 'Fismopink' differs from the male parent, hybrid seedling No. i95/0109/21 (unpatented) in that 'Fismopink' has light pink to white flowers with petal markings that are more purple-red, while the hybrid seedling No. i95/0109/21 has deep violet-pink flowers.

Cultivar 'Fismopink' differs from the commercial comparison variety 'Amri Conred' (U.S. Plant Pat. No. 15,880) in that the petal markings of 'Fismopink' are more purple-red, while the stripes of 'Amri Conred' are about medium red. Additionally, the inflorescences of 'Fismopink' are slightly smaller, but the peduncles are somewhat larger.

I claim:

1. A new and distinct cultivar of *Pelargonium* plant as shown and described herein.

* * * * *